(12) United States Patent  (10) Patent No.: US 6,679,102 B2
Baker                      (45) Date of Patent:    Jan. 20, 2004

(54) METHOD AND APPARATUS FOR MEASURING FLUID CONTAMINANTS

(75) Inventor: Michael Charles Baker, Gretton (GB)

(73) Assignee: Moog Inc., East Aurora, NY (US)

( * ) Notice: Subject to any disclaimer, the term of this patent is extended or adjusted under 35 U.S.C. 154(b) by 0 days.

(21) Appl. No.: 10/200,841

(22) Filed: Jul. 22, 2002

(65) Prior Publication Data

US 2003/0024303 A1 Feb. 6, 2003

(30) Foreign Application Priority Data

Aug. 2, 2001 (GB) .............................................. 0118837

(51) Int. Cl.[7] .............................................. G01N 11/00
(52) U.S. Cl. ..................................................... 73/61.73
(58) Field of Search ........................... 73/61.73, 61.78, 73/865.5, 61.63, 61.65, 61.66, 61.67, 61.68

(56) References Cited

U.S. PATENT DOCUMENTS

| | | | | |
|---|---|---|---|---|
| 3,050,987 A | * | 8/1962 | Osgood .......................... 73/61.73 |
| 4,468,954 A | * | 9/1984 | Lanctot et al. ................... 73/61.73 |
| 4,495,799 A | * | 1/1985 | Fisher et al. .................... 73/61.73 |
| 4,599,893 A | * | 7/1986 | Fisher et al. .................... 73/61.73 |
| 5,349,849 A | * | 9/1994 | Heron ............................ 73/61.73 |
| 6,474,144 B1 | * | 11/2002 | Barnes et al. .................... 73/61.71 |
| 6,549,856 B2 | * | 4/2003 | Baker ............................... 702/50 |

* cited by examiner

Primary Examiner—Michael Cygan
(74) Attorney, Agent, or Firm—Phillips Lytle LLP

(57) ABSTRACT

Apparatus (20) for testing the extent of contaminants in a fluid during a test period, comprises: a source ($P_s$) of pressurized fluid to be tested; a fluid sump (R); a first flow restriction ($R_1$) adapted to be supplied with fluid flow from the source, the first flow restriction being configured as an annular clearance between a first land (24) and a first bore (22) and being sized and arranged so as to be progressively occluded by contaminants in the fluid flow during said test period; a second flow restriction ($R_2$) arranged between the first flow restriction and said sump, the second flow restriction being configured as an annular clearance between a second land (25) and a second bore (22), the second flow restriction being substantially the same dimensionally as the first flow restriction so that the second flow restriction will not be occluded by contaminants passing through the first flow restriction and the pressure drops across each of the flow restrictions will be substantially equal at the beginning of a test period. In use, the improved apparatus performs an improved method.

16 Claims, 1 Drawing Sheet

METHOD AND APPARATUS FOR MEASURING FLUID CONTAMINANTS

TECHNICAL FIELD

The present invention relates generally to methods and apparatuses for sensing and determining the level of contaminants in a fluid, and, more particularly, to improved fluid contaminant measuring apparatuses and methods that closely simulate the physical conditions that such fluid will likely encounter in use.

BACKGROUND ART

This invention provides a fluid contamination measuring apparatus that is closely related to the equipment described in British Patent Application No. 00 17 987.9, which is owned by the assignee of the present application. That system utilizes a contaminant sensing orifice that simulates the annular clearance between a closely-fitted valve spool land and its associated sleeve. The sensing orifice is itself defined between a valve spool land and a bore wall. The valve spool may be selectively moved in an axial direction to align the spool land with a sleeve recess of an enlarged diameter for flushing accumulated contaminant particles from the test orifice prior to the beginning of a test cycle.

The testing technique of exposing an initially-clean test orifice to flow of a contaminated fluid and observing the effect of progressive attenuation of flow as contaminant particles accumulate in the test orifice has apparently been known for many years. Known measurement techniques appear to fall into two broad categories.

In the first, the flow is directly measured, usually by means of a piston. This piston can be used to drive fluid through the test orifice, or to collect fluid passing through the test orifice. In either case, the piston displacement vs. time data enables flow through the orifice to be calculated. Examples of this type are shown in U.S. Pat. Nos. 4,663,966 and 4,495,799 (see FIG. 3 thereof).

In the second category, the test orifice is connected in series with a source of pressurized fluid and a reference orifice having an impedance to flow similar to that of the test orifice. As the test orifice becomes progressively occluded by contaminants, the flow and the pressure drops across the series-connected restrictions will change, providing a basis for calibrating and determining the extent of contamination. An example of this type is shown in U.S. Pat. No. 4,495,799 (see FIGS. 1 and 2 thereof). The '799 patent discloses an arrangement for passing pressurized fluid through an upstream reference orifice, described as a sharp-edged restriction having an opening much larger that the clearance of the annular test orifice, and then through the test orifice itself. A pressure sensing mechanism is then used to measure the pressure drop across the test orifice.

A potential difficulty with this sort of apparatus is that the flow is laminar, and hence sensitive to changes in fluid viscosity and temperature. Pressure drops across the reference and test orifices can be expected to vary in several ways, even in the absence of a contaminant, and can introduce significant errors into the measurement. An attempt to deal with this shortcoming is shown in U.S. Pat. No. 4,685,066, in which a test filter (i.e., a porous disk, rather than an annular orifice) is arranged in series with a similar filter as a reference restriction. The upstream test filter will collect and accumulate particulate contamination, and the downstream filter will pass any particles that have passed through the test filter. Both elements will tend to have the same temperature sensitivity. Hence, that factor can be eliminated as a factor in the testing protocol.

DISCLOSURE OF THE INVENTION

With parenthetical reference to the corresponding parts, portions or surfaces of the disclosed embodiment, merely for purposes of illustration and not by way of limitation, the present invention broadly provides improved methods and apparatuses for determining the extent of contaminants in a fluid.

In one aspect, apparatus (20) for testing the extent of contaminants in a fluid during a test period, comprises: a source of pressurized fluid ($P_s$) to be tested; a fluid sump (R); a first flow restriction ($R_1$) adapted to be supplied with fluid flow from the source, the first flow restriction being configured as an annular clearance between a first land (24) and a first bore (22) and being sized and arranged so as to be progressively occluded by contaminants in the fluid flow during the test period; a second flow restriction ($R_2$) arranged between the first flow restriction and the sump, the second flow restriction being configured as an annular clearance between a second land (25) and a second bore (22), the second flow restriction being substantially the same dimensionally as the first flow restriction so that the second flow restriction will not be occluded by contaminants passing through the first flow restriction and the pressure drops across each of the flow restrictions will be substantially equal at the beginning of a test period.

In this form, as the first flow restriction ($R_1$) becomes progressively occluded by contaminants in the fluid flow during the test period, the pressure drop across the first flow restriction will increase and the pressure drop across the second flow restriction ($R_2$) will decrease, such that the extent of contamination in the fluid will be indicated as a function of a change in pressure or as a change in the ratio of the pressure drops.

The apparatus may include a pressure sensor (45) operatively arrange to measure the fluid pressure between the first and second flow restrictions, such that the extent of contamination in the fluid will be indicated as a function of a change in such sensed pressure.

The flow restriction lands (24, 25) may be provided on a first valve spool (21) movably mounted in a first bore and adapted to be moved in one axial direction relative to the first bore to allow the flow restrictions to be flushed of contaminants prior to the commencement of a test period.

In another aspect, the second land (61) may be provided on a second valve spool movably mounted in a second bore (63). This second flow restriction ($R_2$) may have a substantially-constant radial clearance and a variable axial length ($L_2$). The second flow restriction may have an impedance to flow that is a function of the extent to which the second land overlaps the second bore. The apparatus may further include a sensor (72) for sensing the length of the second flow restriction.

The length of overlap ($L_2$) between the second land and the second bore may be arranged to be selectively increased during the test period so as to cause the pressure drop across the second flow restriction to be maintained substantially equal to the pressure across the first flow restriction as the first flow restriction becomes progressively occluded, such that the extent of contamination in the fluid will be indicated as a function of the length of the overlap.

The second spool may be similarly adapted to be moved in one axial direction relative to the second bore to allow the second flow restriction to be flushed of contaminants prior to the commencement of a test period. The apparatus may include a regulator (56) operatively arranged to change the impedance of the second flow restriction so that the fluid pressure between the flow restrictions will remain substantially constant, such that the extent of contamination in the fluid will be indicated as a function of the change of impedance of the second flow restriction.

In another aspect, the invention provides a method of testing the extent of contaminants in a fluid during a test period, comprising the steps of: providing a source of pressurized fluid to be tested; providing a fluid sump; providing a first flow restriction configured as an annular clearance between a first land and a first bore; causing fluid from the source to flow through the first flow restriction; progressively occluding the first flow restriction with contaminants in the fluid flowing therethrough; providing a second flow restriction between the first flow restriction and the sump, the second flow restriction being configured as an annular clearance between a second land and a second bore and being sized so as to not be occluded by contaminants passing through the first flow restriction; and monitoring the fluid pressure between the first and second flow restrictions; thereby to indicated the extent of contaminants in the source fluid as a function of the change in such monitored pressure during the test period.

According to this method, accumulated contaminants may be removed or flushed from the first flow restriction prior to the beginning of the test period.

In still another aspect, the invention provides a method of testing the extent of contaminants in a fluid during a test period, comprising the steps of: providing a source of pressurized fluid to be tested; providing a fluid sump; providing a first flow restriction configured as an annular clearance between a first land and a first bore; causing fluid from the source to flow through the first flow restriction; progressively occluding the first flow restriction with contaminants in the fluid flowing therethrough; providing a second flow restriction between the first flow restriction and the sump, the second flow restriction being configured as an annular clearance between a second land and a second bore; and varying the impedance of the second flow restriction as a function of the fluid pressure between the first and second flow restrictions; thereby to indicate the extent of contaminants in the source fluid as a function of the change in impedance of the second flow restriction during the test period.

Accordingly, the general object of this invention is to provide improved apparatus for measuring the extent of contaminants in a fluid.

Another object is to provide improved fluid contaminant testing apparatus which closely simulates the physical configuration of apparatus that will be encountered in use.

Another object is to provide improved fluid contaminant testing apparatus in which the extent to contaminants is determined as a function of a change in pressure.

Another object is to provide an improved fluid contaminant testing apparatus in which the extent of contaminants is determined as a function of position.

Still another object is to provide improved methods for testing the level of contaminants in a fluid.

These and other objects and advantages will become apparent from the foregoing and ongoing written specification, the drawings and the appended claims.

DESCRIPTION OF THE PREFERRED EMBODIMENTS

Figure 1:
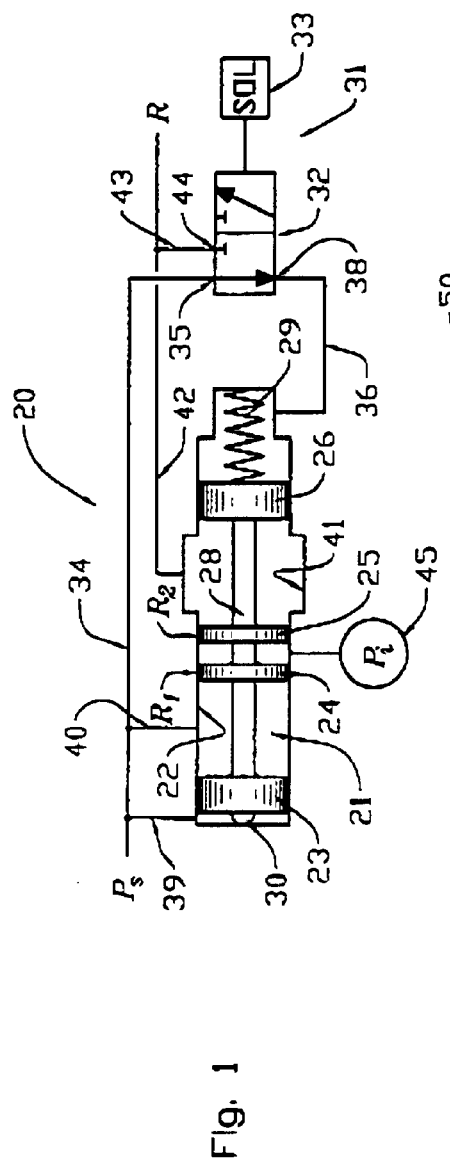
FIG. 1 is a schematic view of a first form of the improved apparatus, showing means for measuring the pressure between the testing and reference orifices.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

First Embodiment (FIG. 1)

Referring now to the drawings, and, more particularly, to FIG. 1 thereof, the invention provides, in one aspect, an improved apparatus, generally indicated at 20, for sensing the level or extent of contaminants in a fluid. Apparatus 20 is shown as broadly including a multi-lobed valve spool, generally indicated at 21, which is mounted for sealed sliding axial movement within a cylindrical body bore 22. Spool 21 is shown as having a leftward support land 23, a test land 24, a reference land 25, and a rightward support land 26. The various lands are connected by a common shaft 28. The radial clearance between each outwardly-facing cylindrical surface of left and right support lands 23, 26 and the facing bore wall surface 22 is typically about one micron. The radial clearance between each outer cylindrical surface of the intermediate testing and reference lands 24, 25, respectively, and the facing bore wall 22 may be on the order of five microns, depending on the expected size of the contaminant particles. A spring 29 is arranged in the spool right end chamber, and continuously urges the valve spool 21 to move leftwardly within bore 22 until a nose 30 at the left end of the spool abuts the rightwardly-facing wall of the spool left end chamber.

A two-position solenoid valve, generally indicated at 31, is shown as having a hydraulic portion 32 and an electrical actuator portion 33. Pressurized fluid (containing contaminants) is arranged to be supplied from a source $P_s$ via conduit 34 to solenoid port 35. A conduit 36 communicates solenoid port 38 with the spool right end chamber containing spring 29. Branch conduits 39 and 40 communicate conduit 34 with the spool left an end chamber and with the annular space between lobes 23 and 24, respectively.

The bore wall is shown as having a portion 41 of an enlarged diameter between lands 25 and 26. This bore portion communicates with return R via a conduit 42. Conduit 43 communicates conduit 42 with solenoid port 44. A pressure gauge, labeled $P_i$, is generally indicated at 45.

This pressure gauge is operatively arranged to normally measure the pressure between the testing and reference lands 24, 25, respectively.

At the beginning of a test cycle, the solenoid actuator 33 is operated so as to displace the solenoid's hydraulic section 32 to the alternative position. In this alternative position, the spool right end chamber communicates with return R via connected conduits 36, 43 and 42. Supply pressure is provided to the spool left end chamber, and drives the valve spool 21 rightwardly such that the two lands 24, 25, are arranged in the large-diameter portion 41 of the bore. This allows contaminants to be flushed from the orifices defined between the two lands and bore wall 22 prior to the commencement of a test cycle.

Thereafter, solenoid 33 is operated to return its hydraulic section to the position shown in FIG. 1. Supply pressure will be provided to the spool right end chamber via communicating conduits 34, 36. Supply pressure is continuously provided to the spool left end chamber via conduits 34, 39. However, since the support lands 23, 26 have the same circular area, and are exposed to the same pressures in their respective end chambers, spring 29 will expand to urge the valve spool to move leftwardly until nose 30 abuts the end wall of the left spool end chamber.

Fluid will then flow from the source through conduits 34, 40 to the annular space between left support land 23 and testing land 24. Such fluid will then flow sequentially through the testing orifice defined between the testing land 24 and the bore wall, and through the reference orifice defined between reference land 25 and the bore wall, into the space between lands 25, 26. From this chamber, fluid will flow to return via conduit 42. The testing and reference lands 24, 25, respectively, are carefully machined to be physically the same. That is to say that they have the same axial length and have the same outer dimension. Hence, the axial length and radial clearance of the two annular orifices ($R_1$, $R_2$) defined between lands 24, 25 and bore wall 22 will be the same. At the beginning of each test cycle, the intermediate pressure determined by pressure sensor 45 will be one-half of the differential between the supply and return pressures.

As flow continues during the test cycle, contaminants in the supplied fluid will begin to accumulate at the test orifice ($R_1$) between land 24 and bore wall 22. Any contaminants that have passed through this orifice will necessarily pass through the second orifice defined between reference land 25 and bore wall 22 since the second orifice is geometrically the same as the first orifice. In effect, the first orifice acts as a filter that captures and accumulates contaminants in the test fluid. As the contaminants accumulate in the testing orifice, the pressure drop across this orifice will increase, the intermediate pressure determined by sensor 45 will decrease, and the pressure drop across the reference orifice ($R_2$) will similarly decrease. Thus, flow through the test and reference orifices is the same, and the apparatus shown in FIG. 1 is relatively insensitive to variations in fluid temperature and viscosity. The change in the intermediate pressure, or, better still, the change in the ratio of the intermediate pressure to the supply pressure (i.e., $P_i/P_s$), therefore provides for an indication of the extent of contamination in the fluid.

At the end of the test cycle, the solenoid may be operated to displace valve spool 21 so as to allow contaminants to be flushed from the reference orifice prior to the commencement of the next cycle.

Figure 2:
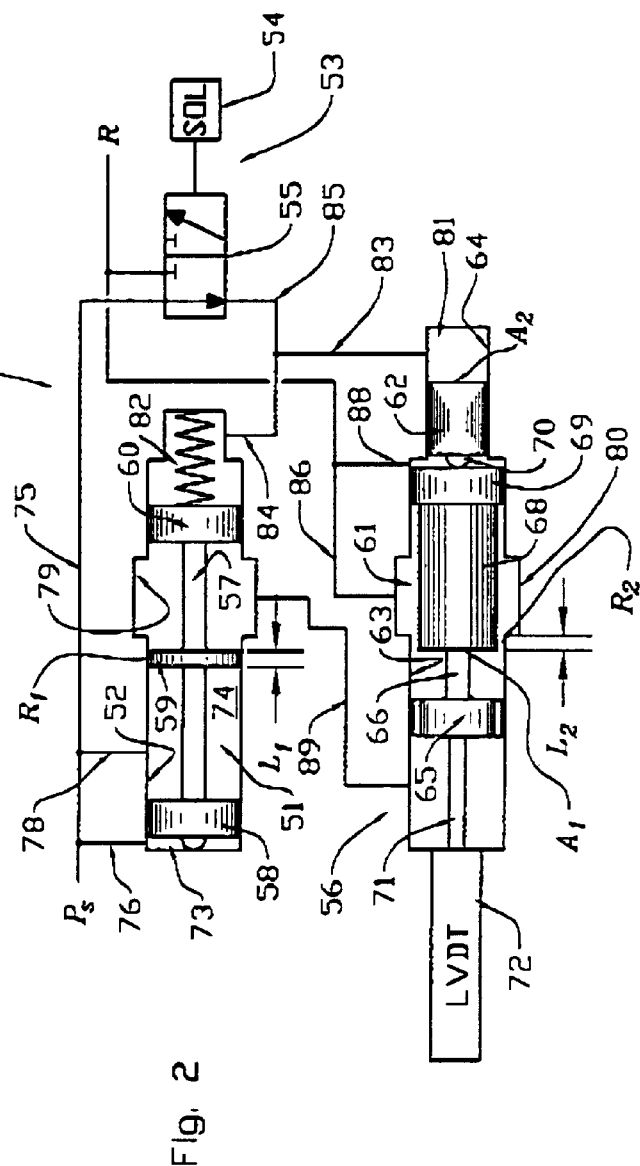
FIG. 2 is a schematic view of a second form of the improved apparatus, showing a regulator for maintaining substantially constant the pressure between the testing and reference orifices.

Second Embodiment (FIG. 2)

A second embodiment of the improved apparatus is shown in FIG. 2. The improved apparatus, generally indicated at 50, is shown as broadly including a main valve spool 51 slidably mounted within a main body bore 52; a solenoid valve 53 having an electrical section 54 and a hydraulic section 55; and a regulator, generally indicated at 56.

The valve spool is shown as including a leftward support land 58, an intermediate sensing land 59 and a rightward support land 60. The radial clearance between each left and right support land 58, 60, respectively, and the facing bore wall 52 is typically on the order of one micron. As before, the radial clearance between intermediate sensing land 59 and the bore wall 52 is on the order of five microns. The various lobes are connected by a common stem 57.

Regulator 56 is shown as having a spool 61 and a displaceable piston 62 mounted within bores 63, 64, respectively. More particularly, the regulator spool 61 is shown as having a leftward support land 65, an intermediate stem 66, an axially-elongated restricting land 68, and a rightward support land 69. Piston 62 is arranged in the smaller-diameter bore wall portion 64 of the body. This piston 62 has a leftward rounded nose 70 which is adapted to selectively engage the right end face of spool 61. A rod 71 communicates the axial position of regulator spool 61 to a Linear Variable Differential Transformer ("LVDT") 72.

Supply pressure is provided from a suitable source $P_s$ to main spool left end chamber 73 and intermediate chamber 74 via conduit 75 and branch conduits 76, 78, respectively. The main bore has a portion, indicated at 79, of an enlarged diameter. The regulator right end chamber 81 communicates with main valve right end chamber 82 via conduits 83, 84, and with the solenoid valve via conduit 85. Conduit 86 communicates an enlarged-diameter portion 80 of regulator spool bore with the fluid return R. Branch conduit 88 communicates the regulator spool right end chamber with conduit 86 and the fluid return. Restricting land 68 is shown as having a leftward area $A_1$. Piston 62 is shown as having a rightward area $A_2$, which is one-half of area $A_1$. Land 59 is shown as having an overlapped axial length of $L_1$. The second orifice is shown as having an overlapped axial length $L_2$, and an unoccluded radial clearance on the order of about five microns. As with the first embodiment, the radial clearances of the first and second orifices ($R_1$, $R_1$, respectively) are the same, but the length $L_2$ of the second orifice is variable. Conduit 89 communicates the space between lands 59, 60 with the space to the left of land 65, which has scalloped cut-outs in its periphery to allow unrestricted fluid communication to the annular left end face of land 68.

At the beginning of a test cycle, solenoid 53 is operated to shift the main valve spool 51 rightwardly so that sensing land 59 is aligned with enlarged bore portion 79 so as to flush any contaminants from the testing orifice $R_1$ between sensing land 59 and bore wall 52. After this has occurred, the solenoid and spool are returned to the position shown. Hence, fluid flows from the source via conduits 75, 78 to chamber 74 between lands 58, 59, and through the sensing orifice $R_1$ defined between sensing land 59 and bore wall 52, through conduit 89, and through the overlapped portion of land 68 and bore wall 63. From the enlarged-diameter portion, the fluid then flows via conduit 86 to the return. By virtue of the geometrical relationship between the end faces of the spools (i.e., $A_2=\frac{1}{2}A_1$), the pressure in line 89 is continuously driven to equal one-half of the sum of the supply and return pressures [i.e., $P_{89}=(P_s+R)/2$]. In other words, the regulator spool will be driven by any force unbalance between the intermediate pressure on area $A_1$ and the supply pressure on reference piston area $A_2$ to a position where, at the start of a test, $L_2$ will equal $L_1$. As the flow through the test orifice is reduced by contamination build-up, the intermediate pressure will tend to decrease, unbalancing the pressure forces on the regulator spool 61 and causing it to be moved axially within its body bore to increase the overlap $L_2$ of land 68. As a result, the pressure drop across the second orifice with reduced flow will be maintained at approximately one-half of the supply pressure, and will thus equal the pressure drop across the test orifice. The position of second spool 61 relative to its bore is sensed and determined by LVDT 72. Thus, in the second embodiment, the change with time of the regulator spool position signal can be used to calculate the level of contamination in the fluid.

Modifications

The present invention contemplates that many changes and modifications may be made. For example, while it is presently preferred to employ solenoids to selectively displace the valve spool within the body to allow flushing of contaminants from the orifice, other types of mechanisms could be substituted therefor. The various parts and components may be readily changed, as desired. For example, position sensing mechanisms other than a LVDT might alternatively be used. The bore wall may be provided in a body, or in a sleeve or bushing mounted on the body.

Therefore, while two presently preferred forms of the improved contaminant sensing apparatus have been shown and described, and several modifications thereof discussed, persons skilled in this art will readily appreciate that various additional changes and modifications may be made without departing from the spirit of the invention, as defined and differentiated by the following claims.

What is claimed is:

1. Apparatus for testing the extent of contaminants in a fluid during a test period, comprising:
   a source of pressurized fluid to be tested;
   a fluid sump;
   a first flow restriction adapted to be supplied with fluid flow from said source, said first flow restriction being configured as an annular clearance between a first land and a first bore and being sized and arranged so as to be progressively occluded by contaminants in said fluid flow during the test period;
   a second flow restriction arranged between said first flow restriction and said sump, said second flow restriction being configured as an annular clearance between a second land and a second bore, said second flow restriction being substantially the same dimensionally as said first flow restriction so that said second flow restriction will not be occluded by contaminants passing through said first flow restriction and the pressure drops across each of said flow restrictions will be substantially equal at the beginning of a test period.

2. The apparatus as set forth in claim 1 wherein, as said first flow restriction becomes progressively occluded by contaminants in said fluid flow during said test period, the pressure drop across said first flow restriction will increase and the pressure drop across said second flow restriction will decrease, such that the extent of contamination in said fluid will be indicated as a function of a change in the ratio of said pressure drops.

3. The apparatus as set forth in claim 1 wherein the length of overlap between said second land and said second bore is arranged to be selectively increased during said test period so as to cause the pressure drop across said second flow restriction to be maintained substantially equal to the pressure across said first flow restriction as said first flow restriction becomes progressively occluded, such that the extent of contamination in said fluid will be indicated as a function of the change of the length of said overlap.

4. The apparatus as set forth in claim 1 wherein said first land is provided on a first valve spool movably mounted in said first bore.

5. The apparatus as set forth in claim 4 wherein said first spool is adapted to be moved in one axial direction relative to said first bore to allow said first flow restriction to be flushed of contaminants.

6. The apparatus as set forth in claim 1 wherein said second land is provided on a second valve spool movably mounted in said second bore.

7. The apparatus as set forth in claim 6 wherein said second flow restriction has a radial clearance and an axial length, wherein said radial clearance is substantially constant.

8. The apparatus as set forth in claim 7 wherein said second flow restriction has an impedance to flow that is a function of the extent to which said second land overlaps said second bore.

9. The apparatus as set forth in claim 8 and further comprising a sensor for sensing the length of said second flow restriction.

10. The apparatus as set forth in claim 8 and further comprising a regulator operatively arranged to change the impedance of said second flow restriction such that the fluid pressure between said flow restrictions will remain substantially constant, such that the extent of contamination in said fluid will be indicated as a function of the change of impedance of said second flow restriction.

11. The apparatus as set forth in claim 2 and further comprising a pressure sensor operatively arranged to measure the fluid pressure between said first and second flow restrictions, such that the extent of contamination in said fluid will be indicated as a function of a change in such sensed pressure.

12. The method of testing the extent of contaminants in a fluid during a test period, comprising the steps of:
    providing a source of pressurized fluid to be tested;
    providing a fluid sump;
    providing a first flow restriction configured as an annular clearance between a first land and a first bore;
    causing fluid from said source to flow through said first flow restriction;
    progressively occluding said first flow restriction with contaminants in the fluid flowing therethrough;
    providing a second flow restriction between said first flow restriction and said sump, said second flow restriction being configured as an annular clearance between a second land and a second bore and being sized so as to not be occluded by contaminants passing through said first flow restriction; and
    monitoring the fluid pressure between said first and second flow restrictions;
    thereby to indicated the extent of contaminants in said source fluid as a function of the change in such monitored pressure during said test period.

13. The method as set forth in claim 12 wherein accumulated contaminants are removed from said first flow restriction prior to the beginning of said test period.

14. The method of testing the extent of contaminants in a fluid during a test period, comprising the steps of:
    providing a source of pressurized fluid to be tested;
    providing a fluid sump;

providing a first flow restriction configured as an annular clearance between a first land and a first bore;

causing fluid from said source to flow through said first flow restriction;

progressively occluding said first flow restriction with contaminants in the fluid flowing therethrough;

providing a second flow restriction between said first flow restriction and said sump, said second flow restriction being configured as an annular clearance between a second land and a second bore; and varying the impedance of said second flow restriction so as to maintain the fluid pressure between said first and second flow restrictions substantially constant; thereby to indicated the extent of contaminants in said source fluid as a function of the change in impedance of said second flow restriction during said test period.

15. The method as set forth in claim 14 wherein contaminants are removed from said first flow passageway prior to the commencement of said test period.

16. The method as set forth in claim 14 wherein the change in impedance of said second flow restriction is a function of the length of overlap between said second land and said second bore.

\* \* \* \* \*